United States Patent [19]

Neher et al.

[11] 4,347,242

[45] Aug. 31, 1982

[54] HYPOCALCAEMIC PEPTIDES AND PROCESS FOR THEIR MANUFACTURE

[75] Inventors: Robert Neher, Binningen; Bernhard Riniker, Frenkendorf, both of Switzerland

[73] Assignee: Ciba-Geigy Corporation, Ardsley, N.Y.

[21] Appl. No.: 889,066

[22] Filed: Mar. 22, 1978

Related U.S. Application Data

[60] Continuation of Ser. No. 632,928, Nov. 18, 1975, abandoned, which is a continuation of Ser. No. 488,880, Jul. 15, 1974, abandoned, which is a division of Ser. No. 253,077, May 15, 1972, abandoned, which is a continuation of Ser. No. 831,776, Jun. 9, 1969, abandoned.

[51] Int. Cl.$^3$ .................... A61K 37/00; C07C 103/52
[52] U.S. Cl. ............................ 424/177; 260/112.5 T
[58] Field of Search .................. 260/112.5 T; 424/177

[56] References Cited

FOREIGN PATENT DOCUMENTS 1104271 8/1965 United Kingdom ......... 260/112.5 T
1259017 4/1969 United Kingdom ......... 260/112.5 T

OTHER PUBLICATIONS

Hawker, et al., Proc. Nat. Acad. Sci. (USA) 58, 1535–1539 (1967).
Tenenhouse, et al., Proc. Nat. Acad. Sci. (USA) 53, 818–822, 1965.
Putter, et al., "Calcitonin", Heinemann Med. Books London, 1968, pp. 74–76.
Potts, et al., Proc. Nat. Acad. Sci. (USA) 59, 1321–1328, 1968; 58, 328–335, 1967.
Foster, Postgrad. Med. J. 44, 411–422 (1968).
Baghdiantz, et al., Nature, 203, 1027–1028, 1964.
Haymovits, et al., Endocrinology 81, 993–1000, 1967.
M.A. Kumar, et al., J. Endocrin. 1965, 33, 469–475.
Weygand, et al., Chem. Ber. 100, 3838–3840, 1967.
König, et al., Chem. Ber. 101, 681–693, 1968.

*Primary Examiner*—Delbert R. Phillips
*Attorney, Agent, or Firm*—Bruce M. Collins

[57] ABSTRACT

Human calcitonin in the form of four components and process for their isolation from C-cells material.

2 Claims, No Drawings

HYPOCALCAEMIC PEPTIDES AND PROCESS FOR THEIR MANUFACTURE

This is a continuation of application Ser. No. 632,928, filed Nov. 18, 1975 (now abandoned), which is a continuation of Ser. No. 488,880, filed July 15, 1974 (now abandoned), which, in turn, is a division of application Ser. No. 253,007, filed May 15, 1972 (now abandoned), which is a continuation of Ser. No. 831,776, filed June 9, 1969 (now abandoned).

The present invention provides new peptides which lower the blood calcium level, their acid addition salts and complexes and a process for their manufacture. These peptides are human calcitonin whose production in pure form, in form of several active components, has been achieved.

It is known that hypocalcaemic hormones occur in mammals and in humans. The structure of porcine thyrocalcitonin has already been explored; it is a dotriacontapeptide amide containing a cystine disulfide ring at the N-terminus. In view of the great importance of calcitonin in the calcium metabolism and in the formation of bones and in the relevant therapy it is important to have human thyrocalcitonin available in pure form. The manufacture of human calcitonin in pure form from C-cell rich medulla carcinoma of the thyroid gland and from C-cell metastasis material has now been accomplished. The process for the manufacture of human calcitonin is characterized in that medullar carcinoma of the thyroid gland or C-cell metastasis material, which has been degreased, for example with acetone or ether, and may have been first extracted with alcohol or with aqueous trichloroacetic acid, is extracted once or repeatedly with a solvent system containing water and a lower alkanol, at a pH value of about 1 to 6, and the resulting solution is worked up in the usual manner as with porcine thyrocalcitonin, especially by gel chromatography with the use of aqueous formic acid as eluant and by Craig distribution with the use of a solvent system containing n-butanol and acetic acid.

The solvent system used for the extraction contains as lower alkanol, for example, methanol, ethanol, propanol, n-butanol or secondary butanol. The water content of the system may vary, for example, from 4 to 50%, preferably from 5 to 30%. The above-mentioned acid pH value is established, for example, with an inorganic acid such as sulfuric or hydrochloric acid, or with an organic acid such as formic or acetic acid, or with an acid buffer such as acetate of citrate buffer. If desired, the solvent system may contain further organic solvents such as acetone, or organic bases such as pyridine or morpholine, and/or inorganic salts such as sodium chloride. Particularly useful are systems containing n-butanol and acetic acid, especially n-butanol+glacial acetic acid+water (75:7.5:21).

The extraction may be performed in several stages with the same or with different solvent systems.

From the extract the crude product is obtained, for example, by evaporation, lyophilization or precipitation, for instance with acetone or trichloroacetic acid.

The chromotographic purification is advantageously carried out on "Sephadex G-50" or on an equivalent material. The elution is performed, for example, with 0.1 N-formic acid.

As mentioned above, the Craig distribution is most advantageously carried out with systems containing n-butanol and acetic acid, for example n-butanol+glacial acetic acid+water (4:1:5).

The main component of human calcitonin (designated herein as HT-$C_2$) is a dotriacontapeptide amide with the following aminoacid sequence: Lys (1), His (1), Asp (3), Thr (5), Ser (1), Glu (2), Pro (2), Gly (4), Ala (2), ½ Cys (2), Val (1), Met (1), Ile (1), Leu (2), Tyr (1), Phe (3), 4 of the 5 carboxyl side-chains being in amide form. In addition to it, further active components which are referred to below by HT-$C_1$, HT-$C_{11}$ and HT-$C_{21}$ have been isolated in pure form. The aminoacid analysis of HT-$C_1$ is identical with that of HT-$C_2$. Thus, the main component of human calcitonin differs considerably in its aminoacid sequence from that of porcine thyrocalcitonin. When HT-$C_1$ and HT-$C_2$ are enzymatically split with trypsin they form two fragments Tr$_I$ and Tr$_{II}$ having the aminoacid sequence indicated in Table 1 in Example 1.

The components HT-$C_1$, HT-$C_2$, HT-$C_{11}$ and HT-$C_{21}$ are unitary in thin layer chromatography and electrophoresis.

it was found that HT-$C_2$ corresponds to the following structural formula:

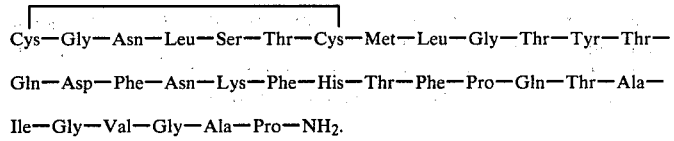

Cys—Gly—Asn—Leu—Ser—Thr—Cys—Met—Leu—Gly—Thr—Tyr—Thr—Gln—Asp—Phe—Asn—Lys—Phe—His—Thr—Phe—Pro—Gln—Thr—Ala—Ile—Gly—Val—Gly—Ala—Pro—$NH_2$.

HT-$C_1$ is the dimer of this compound. From the fact that on dansylation of HT-$C_1$ and acid hydrolysis no bis-dansyl-cystine is formed, one can conclude that HT-$C_1$ is an antiparallel dimer.

Under basic conditions, for example with dilute ammonia, or by reduction, for instance with dimercaptoethanol or dithiothreitol at room temperature in aqueous pyridine, HT-$C_1$ is converted into HT-$C_2$.

The components HT-$C_1$ and HT-$C_2$ can be converted into their sulfoxides by known oxidiation, for example with aqueous hydrogen peroxide. The characteristization of the sulfoxides is shown in the Examples.

Human calcitonin (components HT-$C_1$, HT-$C_2$, HT-$C_{11}$ and HT-$C_{21}$, individually or in any desired mixture) reveals in the rat an activity of about 100 to 200 MRC units per mg (peptide) in the test described by Kumar et al, J. Endocrinology 33, page 470 [1965]. It lowers the plasma calcium level and plasma phosphate level of the blood of mammals, as can be shown by tests on rats weighing 50 to 150 g. In patients with increased bone turn over it lowers the calcium level of the blood on intravenous, intramuscular or subcutaneous injection of 0.01 to 5 mg, for instance in 0.1 molar acetate buffer of pH 4.6. It may therefore be used for the treatment of hypercalcaemiae and of bone diseases such as Paget's disease or osteoporosis.

HT-$C_1$, HT-$C_2$, HT-$C_{11}$ and HT-$C_{21}$ are bases capable of forming acid addition salts with inorganic or organic acids. From the acid addition salts the base can be liberated in known manner. For pharmaceutical purposes the base may be converted into therapeutically acceptable acid addition salts, for example into salts with inorganic acids such as hydrohalic acids, for example hydrochloric or hydrobromic acid, nitric, thiocyanic, sulfuric or phosphoric acid, or with organic acids such as acetic, propionic, stearic, glycollic, lactic, pyruvic, oxalic, citric, benzoic, cinnamic, salicylic, 2-phenoxy- or 2-acetoxy-benzoic acid, mandelic, methanesulfonic, ethanesulfonic, hydroxyethanesulfonic, benzene- or toluenesulfonic, trichloro- or trifluoroacetic acid.

Human calcitonin can be converted in known manner into pharmaceutically useful complexes having a prolonged activity, for example complexes with substances that are known to prolong the activity of peptides, such as nonantigenic gelatin, especially oxypolygelatin, polyvinyl-pyrrolidone, polyphloretinephosphate, phytic acid, protamine, polyglutamic acid or sparingly soluble metal compounds, for example phosphates, pyrophosphates or hydroxides of aluminum, magnesium, cobalt or especially zinc.

The salts and complexes are suitable for the same use as the free peptide.

For use in pharmaceutical preparations the new compounds may be mixed with a pharmaceutical organic or inorganic excipient suitable for enteral of parenteral administration. Suitable excipients are, for example, water, physiological saline solutions, gelatin, lactose, glucose, starches, vegetable oils, benzyl alcohols, polyalkyleneglycols and other known pharmaceutical excipients. The preparations may be sterilized and/or contain assistants such as preservatives, stabilizers, wetting agents or emulsifiers. They may also contain further therapeutically valuable additives.

The following Examples illustrate the invention.

In thin-layer chromatography the following systems are used:

| System | |
|---|---|
| 45 | sec-butanol + 3% aqueous ammonia (7:3) |
| 52 | n-butanol + glacial acetic acid + water (75:7.5:21) |
| 79 | n-butanol + pyridine + water (1:1:1) |
| 101A | n-butanol + pyridine + glacial acetic acid + water (42:24:4:30) |
| 104 | chloroform + methanol + 17% aqueous ammonia (41:41:18) |

Unless otherwise indicated, thin-layer chromatography is carried out on Alox D-O (Messrs. Camag). All values (Rs) are referred to porcine α-thyrocalcitonin sulfoxide = 1.

Electrophoresis is performed on Avicel cellulose or on Cellogel (cellulose acetate films) at pH = 1.9 [with the buffer glacial acetic acid + formic acid + water (95:26.5:980)] at 140 Volt, 2 hours. The distance travelled (d) is referred to porcine α-thyrocalcitonin sulfoxide = 1.

EXAMPLE 1

10 Grams of medulla carcinoma are immediately deep-frozen and lyophilized. The fatty constituents are removed by extraction with either and the dry tissue (2 g) is thoroughly extracted 3 times with 10 times the volume of a mixture of n-butanol + glacial acetic aicd + water (75:7.5:21) at 20° C. The extracts are combined, in vacuo freed from butanol and lyophilized, to yield 450 mg of a dry residue having an activity of 12 MRC units per mg. 300 mg of this product in 0.1 N-formic acid are purified by gel filtration through a column (450 ml) of Bio Gel P6 or Sephadex G-50 in 0.1 N-formic acid. The active fractions (0.5 to 0.7 column volumes) are combined and lyophilized, to yield 18 mg of a product of 50 MRC units per mg. This material is then subjected to a multiplicative distribution in the system glacial acetic acid + water + butanol (1:5:4) over 140 stages, choosing a phase volume of 3 ml at a phase ratio of 1. The active fractions identified by testing are combined in groups of 10 elements each, freed from the solvent and lyophilized. For the fractions with maximum activity K = 0.6. The peptide HT-$C_2$ obtained therefrom is pure according to thin-layer chromatography and electrophoresis. In the rat it displays an activity of about 100–200 MRC units per mg of peptide. The distance travelled, referred to porcine α-thyrocalcitonin sulfoxide, in the system 52 on Alox DO is 1.16; in the system 79 on Alox DO it is 1.79; in the system 104 on Alox DO it is 1.28; in the system 45 on Alox DO it is 1.37. In glacial acetic acid + formic acid + water (95:26.5:980) at pH 1.9 the product travels at 140 volts in 2 hours on Avicel cellulose towards the cathode d = 0.77, referred to porcine α-thyrocalcitonin sulfoxide = 1.

The produce gives positive color reactions with ninhydrin, chlorotolidine, potassium hexacyanoferrate (II)-iron (III) chloride, diazotized sulfanilic acid amide, no reaction with 4-dimethylaminobenzaldehyde-hydrochloric acid or Sakaguchi reagent; no ultraviolet fluorescence; tryptophan is absent. The aminoacid analysis after acid hydrolysis reveals the following result: Lysine (1), histidine (1), aspartic acid (3), threonine (5), serine (1), glutamic acid (2), proline (2), glycine (4), alanine (2), ½ cystine (2), valine (1), methionine (1), isoleucine (1), leucine (2), tyrosine (1), phenylalanine (3), $NH_3$. The sulfoxide of HT-$C_2$ reveals the following values: Rs 52 = 1.07, Rs 45 = 1.20, Rs 79 = 1.66.

For further characterization the enzymatic splitting of the peptide with trypsin is used. There are obtained two fragments, namely $Tr_I$ containing the aminoacids 1–18, and $Tr_{II}$ with the aminoacids 19–32. The aminoacid sequence of the two fragments is shown in Table 1. $Tr_{II}$ is in thin-layer chromatography on Alox DO distinctly more lipophilic than $Tr_I$ and travels in the electrophoresis faster towards the cathode than does $Tr_I$.

Fragment $Tr_I$: Rs 52 = 0.53; Rs 79 = 0.54; Rs 104 = 0.51. Electrophoresis on Avicel cellulose: d = 0.81.

Fragment $Tr_{II}$: Rs 52 = 1.38; Rs 79 = 1.45; Rs 104 = 1.43. Electrophoresis on Avicel cellulose: d = 0.94.

TABLE 1

| | $Tr_I$ | $Tr_{II}$ |
|---|---|---|
| $NH_3$ | (3) | (2) |
| Lys | 1 | |
| His | | 1 |
| Asp | 3 | |
| Thr | 3 | 2 |
| Ser | 1 | |
| Glu | 1 | 1 |
| Pro | | 2 |
| Gly | 2 | 2 |
| Ala | | 2 |
| ½ Cys | 2 | |
| Val | | 1 |
| Met | 1 | |
| Ile | | 1 |
| Leu | 2 | |
| Tyr | 1 | |
| Phe | 1 | 2 |

TABLE 1-continued

| Tr$_I$ | Tr$_{II}$ |
|---|---|
| 18 | 14 |

EXAMPLE 2

110 Grams of deep-frozen C-cell metastasis material taken from the chest are degreased with ether and then extracted as described in Example 1 with n-butanol+-glacial acetic acid+water (75:7.5:21), to furnish 6 g of dry extract as a dark-brown powder, which is repeatedly agitated with 0.1 N-formic acid (total 150 ml), during which 3.6 g of the dry residue pass into solution. The solution is subjected in two portions on a Bio Gel P6 column (5 cm; 85 cm; volume about 1.6 liter) to gel chromatography with 0.1 N-formic acid and collected in fractions of 20 ml each. There are two peaks with active material present, namely in fractions 13-21 with the peak maximum at 0.4 column volume and the fractions 25-34 with the peak maximum at 0.55 column volume. The fractions 25-34 are combined and lyophilized to furnish 105 mg of crude produce which is identical with the product obtained by gel filtration as described in Example 1 and, after multiplicative distribution according to Example 1, furnishes pure HT-C$_2$. The combined fractions 13-21 are lyophilized and furnish 202 mg of crude product which is subjected to a multiplicative distribution in the system n-butanol+glacial acetic acid+water (4 : 1 : 5) over 400 stages in elements having a phase volume of 3 ml each. The activity maximum is at K=0.19. The resulting pure product (HT-C$_1$) gives in the rat test according to Kumar et al. (see above) about as good results as the product obtained in Example 1 (HT-C$_2$). It can be converted, for example with 5% hydrogenperoxide, into the equally active sulfoxide. In thin-layer chromatography on Alox DO Rs 52=1.04; Rs 79=1.42; Rs 45=1.20. The sulfoxide reveals the following values: Rs 52=0.88; Rs 79=1.29; Rs 45=1.09. In electrophoresis on Avicel cellulose d=0.90 for HT-C$_1$ and its sulfoxide. On Cellogel d=1.15 for HT-C$_1$ and d=1.35 for its sulfoxide. HT-C$_1$ gives positive reactions with ninhydrin, chlorotolidine, Pauly reagent and Barton's reagent. The reaction according to Sakaguchi and according to Ehrlich and ultraviolet fluorescence are negative.

Aminoacid analysis after acid hydrolysis reveals: Lysine (1), histidine (1), aspartic acid (3), threonine (5), serine (1), glutamic acid (2), proline (2), glycine (4), alanine (2), ½ cystin (2), valine (1), methionine (1), isoleucine (1), leucine (2), tyrosine (1), phenylalanine (3), NH$_3$.

By trypsin splitting, two fragments with the same aminoacid sequences as for HT-C$_2$ in Table 1 of Example 1 are obtained. Tr$_{II}$ is identical for HT-C$_1$ and HT-C$_2$.

For fragment Tr$_I$ Rs 52 (on Alox)=0.55; Rs 101 A (on cellulose)=0.86. In electrophoresis on Avicel cellulose d=0.91.

For fragment Tr$_{II}$Rs 52 (on Alox)=1.38; Rs 101 A (on cellulose)=1.31. In electrophoresis on Avicel cellulose d=0.94.

HT-C$_2$ is dissolved in 50 times its own weight of a 0.1% cysteine hydrochloride solution and kept for 1 hour at 45° C., and the solution is then chromatographed. Apart from other products, a spot corresponding to HT-C$_1$ is found.

When HT-C$_1$ is heated with 0.5 N-ammonia for 1 hour at 45° C., it is converted into HT-C$_2$.

EXAMPLE 3

When medulla carcinoma is extracted as described in Example 1, the dry residue is purified by gel filtration and the resulting product (containing 50 MRC units/mg) is subjected to a multiplicative distribution as described in Example 1, there are obtained apart from the fractions with a maximum activity K=0.6 fractions with K=2.7. The peptide HT-C$_{21}$ obtained therefrom is unitary in thin-layer chromatography and electrophoresis. It has the same aminoacid composition as HT-C$_2$, but it has no free α-amino group. It reveals in the rat an activity of about 100-200 MRC units per mg of peptide.

In thin-layer chromatography on Alox DO Rs 52=1.40; Rs 104=1.40; Rs 79=1.80. In the electrophoresis on Avicel cellulose d=0.56.

The product gives positive color reactions with ninhydrin, chlorotolidine, potassium hexacyanoferrate (II)-iron (III) chloride and diazotized sulfanilic acid amide.

EXAMPLE 4

When medulla carcinoma is extracted as described in Example 2, the dry residue of the extract purified by gel filtration and the product of fractions 13-21 is subjected to a multiplicative distribution, there are obtained—apart from the active fractions with K=0.19—fractions with K=4.0. The peptide HT-C$_{11}$ obtained therefrom proves to be unitary in thin-layer chromatography and electrophoresis. In the rat it displays an activity of about 100-200 MRC units per mg of peptide. In thin-layer chromatography on Alox DO Rs 52=1.45; Rs 104=1.60; Rs 79=1.60. In the electrophoresis on Avicel cellulose D=0.54. The product gives positive color reactions with ninhydrin, chlorotolidine, potassium hexacyanoferrate (II)-iron(III)chloride and diazotized sulfanilic acid amide.

EXAMPLE 5

A solution of 0.5 mg of

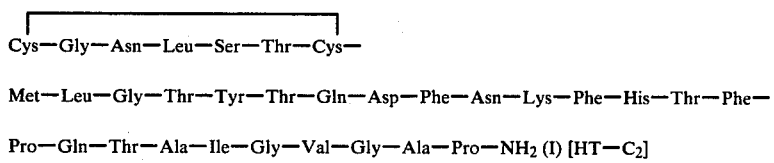

Cys—Gly—Asn—Leu—Ser—Thr—Cys—

Met—Leu—Gly—Thr—Tyr—Thr—Gln—Asp—Phe—Asn—Lys—Phe—His—Thr—Phe—

Pro—Gln—Thr—Ala—Ile—Gly—Val—Gly—Ala—Pro—NH$_2$ (I) [HT—C$_2$]

in 1 ml of an aqueous solution of 20 mg of mannitol and 4.6 mg of formic acid is filtered sterile and under aseptic conditions charged into a 5 ml-ampoule, then deep-cooled and lyophilized. Before use the lyophilizate is dissolved in distilled water. The contents of the ampoule corresponds to about 70 MRC units. The solution is injected intramuscularly or intravenously, for example 10 to 70 MRC-units per day.

EXAMPLE 6

A suspension is prepared by dissolving 5.25 mg of $ZnCl_2$ and 1.05 mg of $Na_2HPO_4.2H_2O$ in 0.5 ml of 0.1 N hydrochloric acid, adding with stirring a solution of 1.0 mg of calcitonin M-HT-$C_2$ in 0.25 ml of distilled water, then 0.5 N NaOH up to pH 8.6 and filling up to 1 ml with distilled water. The suspension corresponds to about 150 MRC-units. It can be preserved with a suitable preservative, for instance with 10 mg of benzyl alcohol.

The suspension can be used for intramuscular injection, for example 25 to 75 MRC units per day.

We claim:

1. The dotriacontapeptide amide of the formula

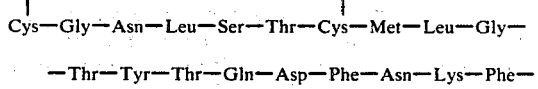
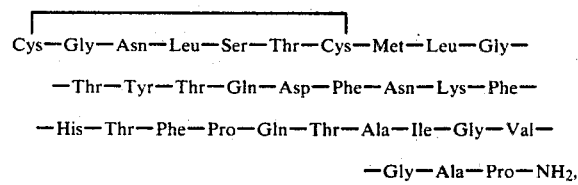

its acid addition salts and complexes.

2. A pharmaceutical preparation suitable for treatment of hypercalcaemia, Paget's disease and osteoporosis comprising an effective amount of the dotriacontapeptide amide of the formula Cys—Gly—Asn—Leu—Ser—Thr—Cys—Met—Leu—Gly—

—Thr—Tyr—Thr—Gln—Asp—Phe—Asn—Lys—Phe—

—His—Thr—Phe—Pro—Gln—Thr—Ala—Ile—Gly—Val—

—Gly—Ala—Pro—NH$_2$, as claimed in claim 1, or its acid addition salts or complexes in a pharmaceutical excipient suitable for enteral or parenteral administration.

* * * * *